(12) United States Patent
Hwang et al.

(10) Patent No.: US 7,449,420 B2
(45) Date of Patent: Nov. 11, 2008

(54) PRODUCTION OF ALKYL AROMATIC COMPOUNDS WITH CATALYST REACTIVATION

(75) Inventors: Shyh-Yuan Henry Hwang, Newton, MA (US); Waheed A. Mukaddam, Cambridge, MA (US); Francis A. Demers, Holderness, NH (US); Dana Johnson, Hopkinton, MA (US)

(73) Assignee: Stone & Webster Inc., Houston, TX (US)

( * ) Notice: Subject to any disclaimer, the term of this patent is extended or adjusted under 35 U.S.C. 154(b) by 1060 days.

(21) Appl. No.: 10/804,459

(22) Filed: Mar. 19, 2004

(65) Prior Publication Data

US 2004/0242404 A1    Dec. 2, 2004

Related U.S. Application Data

(60) Provisional application No. 60/457,084, filed on Mar. 21, 2003.

(51) Int. Cl.
*B01J 20/34* (2006.01)
(52) U.S. Cl. ............................. 502/31; 502/56
(58) Field of Classification Search ............... 502/20, 502/31, 34, 56
See application file for complete search history.

(56) References Cited

U.S. PATENT DOCUMENTS

| | | | |
|---|---|---|---|
| 3,751,504 A | 8/1973 | Keown et al. |
| 3,851,004 A | 11/1974 | Yang |
| 4,016,218 A | 4/1977 | Haag et al. |
| 4,049,739 A | 9/1977 | Zabransky et al. |
| 4,086,287 A | 4/1978 | Kaeding et al. |
| 4,100,217 A | 7/1978 | Young |
| 4,104,319 A | 8/1978 | Kaeding |
| 4,117,020 A | 9/1978 | Sun |
| 4,143,084 A | 3/1979 | Kaeding et al. |
| 4,169,111 A | 9/1979 | Wight |
| 4,459,426 A | 7/1984 | Inwood et al. |
| 4,547,605 A | 10/1985 | Kresge et al. |
| 4,822,943 A | 4/1989 | Burress |
| 4,849,569 A | 7/1989 | Smith, Jr. |
| 4,857,666 A | 8/1989 | Barger et al. |
| 4,891,458 A | 1/1990 | Innes et al. |
| 4,908,341 A | 3/1990 | Pruden et al. |
| 4,950,834 A | 8/1990 | Arganbright et al. |
| 4,954,325 A | 9/1990 | Rubin |
| 4,982,030 A | 1/1991 | Kaeding et al. |
| 4,992,606 A | 2/1991 | Kushnerick et al. |
| 5,004,841 A | 4/1991 | Lee et al. |
| 5,012,021 A | 4/1991 | Vora et al. |
| 5,021,141 A | 6/1991 | Rubin |
| 5,030,786 A | 7/1991 | Shamshoum et al. |
| 5,077,445 A | 12/1991 | Le |
| 5,081,323 A | 1/1992 | Innes et al. |
| 5,086,193 A | 2/1992 | Sy |
| 5,113,031 A | 5/1992 | Sy |
| 5,118,897 A | 6/1992 | Khonsari et al. |
| 5,146,026 A | 9/1992 | Tejero et al. |
| 5,157,185 A | 10/1992 | Chu et al. |
| 5,160,497 A | 11/1992 | Juguin et al. |
| 5,175,135 A | 12/1992 | Lee et al. |
| 5,198,595 A | 3/1993 | Lee et al. |
| 5,212,128 A | 5/1993 | Schorfheide et al. |
| 5,215,725 A | 6/1993 | Sy |
| 5,236,575 A | 8/1993 | Bennett et al. |
| 5,240,889 A | 8/1993 | West et al. |
| 5,250,277 A | 10/1993 | Kresge et al. |
| 5,258,565 A | 11/1993 | Kresge et al. |
| 5,292,698 A | 3/1994 | Chu et al. |
| 5,306,681 A | 4/1994 | Schorfheide et al. |
| 5,334,795 A | 8/1994 | Chu et al. |
| 5,362,697 A | 11/1994 | Fung et al. |
| 5,371,310 A | 12/1994 | Bennett et al. |
| 5,430,211 A | 7/1995 | Pogue et al. |
| 5,437,855 A | 8/1995 | Valyocsik |
| 5,453,554 A | 9/1995 | Cheng et al. |
| 5,493,065 A | 2/1996 | Cheng et al. |
| 5,522,984 A | 6/1996 | Gajda et al. |

(Continued)

FOREIGN PATENT DOCUMENTS

EP    0 353 813 B1    2/1990

(Continued)

*Primary Examiner*—Edward M Johnson
(74) *Attorney, Agent, or Firm*—Locke Lord Bissell & Liddell, LLP; Alan B. Clement

(57) ABSTRACT

Improved processes are provided for the production of alkyl aromatic compounds using zeolite catalyst(s) and for periodic reactivation in situ of zeolite catalyst(s) that have at least in part become deactivated. Processes according to this invention are typically carried out in a reaction section loaded with catalyst(s) wherein a desired alkyl aromatic compound is produced from feed aromatic and olefin compounds followed by a separation section in which the desired product is isolated and recovered. Alkylation, transalkylation, and/or isomerization reactions that occur in the reaction section are carried out in liquid phase or partial liquid phase over the said zeolite catalyst(s). At least a portion of the zeolite catalyst(s) employed in the reaction section is (are) reactivated in situ, periodically or when deemed necessary, by contacting the deactivated catalyst(s), at elevated temperature and in the substantial absence of olefin feedstock, with an aromatic stripping stream comprising the feed aromatic compound, the desired alkyl aromatic product, byproducts formed in the process, or mixtures thereof, to restore its (their) activity.

29 Claims, No Drawings

U.S. PATENT DOCUMENTS

| | | |
|---|---|---|
| 5,530,170 A | 6/1996 | Beck et al. |
| 5,536,894 A | 7/1996 | Degnan et al. |
| 5,557,024 A | 9/1996 | Cheng et al. |
| 5,563,311 A | 10/1996 | Chang et al. |
| 5,569,805 A | 10/1996 | Beck et al. |
| 5,672,799 A | 9/1997 | Perego et al. |
| 5,689,025 A | 11/1997 | Abichandani et al. |
| 5,811,613 A | 9/1998 | Bhat et al. |
| 5,900,520 A | 5/1999 | Mazzone et al. |
| 5,902,917 A | 5/1999 | Collins et al. |
| 5,907,073 A | 5/1999 | Ghosh |
| 5,980,859 A | 11/1999 | Gajda et al. |
| 6,049,018 A | 4/2000 | Calabro et al. |
| 6,051,521 A | 4/2000 | Cheng et al. |
| 6,060,632 A | 5/2000 | Takamatsu et al. |
| 6,096,935 A | 8/2000 | Schulz et al. |
| 6,162,416 A | 12/2000 | Gajda et al. |
| 6,232,515 B1 | 5/2001 | Schulz et al. |
| 6,281,399 B1 | 8/2001 | Schulz et al. |
| 6,313,362 B1 | 11/2001 | Green et al. |
| 6,479,721 B1 | 11/2002 | Gajda et al. |
| 6,525,234 B1 | 2/2003 | Dandekar et al. |

FOREIGN PATENT DOCUMENTS

| | | |
|---|---|---|
| EP | 0 467 007 B1 | 1/1992 |
| JP | 56133224 | 10/1981 |
| WO | WO 01/83408 A1 | 11/2001 |
| WO | WO 02/26671 A1 | 4/2002 |
| WO | WO 02/062734 A1 | 8/2002 |
| WO | WO 03/006160 A1 | 1/2003 |

PRODUCTION OF ALKYL AROMATIC COMPOUNDS WITH CATALYST REACTIVATION

CROSS REFERENCE TO RELATED APPLICATIONS

The present invention claims priority from U.S. Provisional Application Ser. No. 60/457,084, filed Mar. 21, 2003.

BACKGROUND OF THE INVENTION

Catalytic reaction of aromatic and olefins in the presence of acidic zeolite catalysts has been used in most of the advanced chemical processes for the production of alkyl aromatic compounds such as cumene and ethylbenzene. Since the early 1990s, new zeolite-based cumene technologies have been developed by Mobil/Badger, Dow/Kellogg, UOP and others. These cumene technologies carry out the alkylation of benzene with propylene in liquid phase in the presence of a solid acidic zeolite catalyst. A process developed by CDTech effects alkylation of benzene and propylene in mixed phases in a catalytic distillation column that houses both distillation devices and bales of zeolite catalysts.

Catalysts that can be used for alkylation of benzene with propylene and also for transalkylation of benzene and poly-isopropylbenzenes in liquid phase include zeolite beta, zeolite Y, zeolite omega, ZSM-5, ZSM-12, MCM-22, MCM-36, MCM-49, MCM-56, MCM-58, MCM-68, faujasite, mordenite, porous crystalline magnesium silicates and tungstate modified zirconia, all of which are known in the art.

MCM-22 and its use to catalyze the synthesis of alkyl aromatics are described, for example, in U.S. Pat. No. 4,954,325 (Rubin), U.S. Pat. No. 4,992,606 (Kushnerick), U.S. Pat. No. 5,077,445 (Le), U.S. Pat. No. 5,334,795 (Chu) and U.S. Pat. No. 5,900,520 (Mazzone). MCM-36 and its use in the synthesis of alkyl aromatics are described in U.S. Pat. No. 5,250,277 (Kresge), U.S. Pat. No. 5,292,698 (Chu) and U.S. Pat. No. 5,258,565 (Kresge). MCM-49 and its use in the synthesis of alkyl aromatics are described in U.S. Pat. No. 5,236,575 (Bennett), U.S. Pat. No. 5,493,065 (Cheng) and U.S. Pat. No. 5,371,310 (Bennett). MCM-56 and its use to catalyze the synthesis of alkyl aromatics are described in U.S. Pat. No. 5,362,697 (Fung), U.S. Pat. No. 5,453,554 (Cheng), U.S. Pat. No. 5,536,894 (Degnan), U.S. Pat. No. 5,557,024 (Cheng) and U.S. Pat. No. 6,051,521 (Cheng). MCM-58 and its use for the production of alkyl aromatics are described in U.S. Pat. No. 5,437,855 (Valyocsik) and U.S. Pat. No. 5,569,805 (Beck). MCM-68 and its use for the production of alkyl aromatics are described in U.S. Pat. No. 6,049,019 (Calabro).

The use of tungstate-modified zirconia to catalyze the synthesis of alkyl aromatics is described in U.S. Pat. No. 5,563,311 (Chang). U.S. Pat. No. 5,081,323 (Innes) teaches a liquid phase alkylation or transalkylation process using zeolite beta. Production of cumene over zeolite Y is described in U.S. Pat. No. 5,160,497 (Juguin) and U.S. Pat. No. 5,240,889 (West). U.S. Pat. No. 5,030,786 (Shamshoum) and U.S. Pat. No. 5,980,859 (Gajda) and European Patent No. 0 467 007 (Butler) describe the production of alkyl aromatic compounds with zeolite Beta, zeolite Y and zeolite Omega. U.S. Pat. No. 5,522,984 (Gajda), U.S. Pat. No. 5,672,799 (Perego), U.S. Pat. No. 5,980,859 (Gajda) and U.S. Pat. No. 6,162,416 (Gajda), teach the production of cumene with zeolite beta. Use of zeolite mordenite in production of monoalkylated benzenes, such as cumene and ethylbenzene, is described in U.S. Pat. No. 5,198,595 (Lee). Production of ethylbenzene with ex situ selectivated zeolite catalyst is described in U.S. Pat. No. 5,689,025 (Abichandani).

The first zeolite-based ethylbenzene process, developed jointly by Mobil and Badger in the early 1980s, utilized vapor phase alkylation of benzene with ethylene and vapor phase transalkylation of benzene and polyethylbenzene. Both the alkylation and transalkylation steps of this early process were carried out in the presence of solid acidic ZSM-5 catalysts. Production of ethylbenzene with ZSM-5 is described in U.S. Pat. No. 5,175,185 (Chu). Several liquid phase zeolite-based ethylbenzene technologies were developed in the late 1980s and in the 1990s by UOP/Lummus, Mobil/Badger and others. Alkylation of benzene with ethylene and transalkylation of benzene and polyethylbenzenes were carried out in the liquid phase in the presence of solid acidic zeolite catalysts. Catalysts that can be used for alkylation of benzene with ethylene and transalkylation of benzene and polyethylbenzenes in liquid phase processes include zeolite beta, zeolite Y, zeolite omega, ZSM-5, ZSM-12, MCM-22, MCM-36, MCM-49, MCM-56, MCM-58, MCM-68, faujasite, mordenite, porous crystalline magnesium silicates and tungstate-modified zirconia. A process developed by CDTech effects alkylation of benzene and ethylene in mixed phases in a catalytic distillation column that houses both distillation devices and bales of zeolite catalysts.

Production of ethylbenzene over intermediate pore size zeolites is described in U.S. Pat. No. 3,751,504 (Keown), U.S. Pat. No. 4,547,605 (Kresge) and U.S. Pat. No. 4,016,218 (Haag). U.S. Pat. No. 4,169,111 (Wight) and U.S. Pat. No. 4,459,426 (Inwood) disclose production of ethylbenzene over large pore size zeolites, such as zeolite Y. Synthesis of zeolite ZSM-12 is described in U.S. Pat. No. 5,021,141 (Rubin). A process for ethylbenzene production over zeolite ZSM-12 is described in U.S. Pat. No. 5,907,073 (Kumar). Production of ethylbenzene over zeolite mordenite is described in U.S. Pat. No. 5,430,211 (Pogue). Liquid phase synthesis of ethylbenzene with zeolite beta is described in U.S. Pat. No. 4,891,458 (Innes) and U.S. Pat. No. 6,060,632 (Takamatsu). U.S. Pat. No. 4,849,569 (Smith), U.S. Pat. No. 4,950,834 (Arganbright), U.S. Pat. No. 5,086,193 (Sy), U.S. Pat. No. 5,113,031 (Sy) and U.S. Pat. No. 5,215,725 (Sy) teach various systems for catalytic distillation production of alkylated aromatic compounds, including ethylbenzene and cumene.

U.S. Pat. No. 5,902,917 (Collins) teaches a process for producing alkyl aromatics, especially ethylbenzene and cumene, wherein a feedstock first is fed to a transalkylation zone and the entire effluent from the transalkylation zone then is cascaded directly into an alkylation zone along with an olefin alkylating agent, especially ethylene or propylene.

U.S. Pat. No. 6,096,935 (Schulz) teaches a process for producing alkyl aromatics using a transalkylation reaction zone and an alkylation reaction zone. The transalkylation reaction zone effluent passes to the alkylation reaction zone where aromatics in the transalkylation reaction zone effluent are alkylated to the desired alkyl aromatics. U.S. Pat. Nos. 6,232,515 and 6,281,399 (Schulz) teach further details of processes for producing ethyl and isopropyl aromatics using a transalkylation reaction zone and an alkylation reaction zone.

U.S. Pat. No. 6,313,362 (Green) teaches an aromatic alkylation process in which the alkylation product is contacted with a purification medium in a liquid phase pre-reaction step to remove impurities and to form a purified stream. The purified stream then may be processed further by liquid phase transalkylation to convert the polyalkylated aromatic compound to a monoalkylated aromatic compound. The process may use a large pore molecular sieve catalyst, such as MCM-22, as the purification medium in the pre-reaction step because of its high reactivity for alkylation, strong retention of catalyst poisons and low reactivity for oligomerization under the pre-reactor conditions. Olefins, diolefins, styrene, oxygenated organic compounds, sulfur-containing compounds, nitrogen-containing compounds and oligomeric compounds are claimed to be removed by this process.

U.S. Pat. No. 6,479,721 (Gajda) teaches a process for the alkylation of aromatics with olefins using a solid catalyst wherein the olefin ratio and/or the maximum olefin concentration in the alkylation catalyst bed is maintained less than an upper limit to reduce the catalyst deactivation rate and the formation of diphenylalkanes.

PCT published application WO02062734 (Chen) teaches a process for producing a monoalkylation aromatic product, such as ethylbenzene and cumene, utilizing an alkylation zone and a transalkylation zone in series or a combined alkylation and transalkylation reactor zone. This invention claims to minimize the amount of excess aromatic material that is used and needs to be recovered and subsequently recirculated, thus minimizing the production cost.

Processes for production of dialkyl aromatic compounds over zeolite catalysts are taught in numerous patent documents. For example, U.S. Pat. Nos. 4,086,287, 4,104,319, 4,143,084 and 4,982,030 (Kaeding) teach the production of dialkyl substituted benzenes, such as para-ethyltoluene and para-diethylbenzene, by selective ethylation of mono alkyl benzenes, such as toluene and ethylbenzene, over crystalline aluminosilicate zeolite catalysts, such as ZSM-5, ZSM-5 modified with an oxide of magnesium and ZSM-5 modified with an oxide of magnesium and an oxide of phosphorus. U.S. Pat. No. 4,100,217 (Young) teaches a process for selective production of para-substituted benzenes, such as para-xylene, para-ethyltoluene and para-diethylbenzene, wherein toluene or ethylbenzene is reacted with a methylating or ethylating agent in the presence of a catalyst that consists essentially of ZSM-23.

U.S. Pat. No. 4,117,020 (Sun) teaches a process to recover valuable alkylated aromatic hydrocarbons from a tar comprising a fraction of an alkylation reaction product distilling above about 240° C. by contacting the tar with benzene and/or toluene in the presence of a catalytic amount of a crystalline aluminosilicate molecular sieve catalyst. The invention is said to be effective in recovering ethylbenzene and diethylbenzenes by contacting the tar resulting from benzene alkylation with ethylene in the presence of aluminum chloride with benzene in the presence of zeolite Y molecular sieve at a temperature of at least about 240° C. and at a pressure of at least about 200 psi. U.S. Pat. No. 5,530,170 (Beck) teaches a process for the alkylation of ethylbenzene with ethylene to selectively produce para-diethylbenzene over a zeolite catalyst, such as ZSM-5, which has been selectivated by multiple treatments with a siliceous material. U.S. Pat. No. 5,811,613 (Bhat) teaches a process for single step alkylation of ethylbenzene with ethanol in the presence of gallo aluminosilicate zeolite catalyst. The product para-diethylbenzene can be recovered directly from the reactor effluent by simple distillation.

Similarly, several patent documents describe processes of producing diisopropylbenzenes over various zeolite catalysts. A Japanese patent document, 56133224 (Tetsuo), teaches a process to obtain selectively a diisopropylbenzene isomeric mixture with a high para-diisopropylbenzene content by alkylating cumene with alkylating agent selected from an olefin, an alcohol and an alkyl halide in the vapor phase in the presence of a catalyst consisting of either: (a) an acid extraction mordenite zeolite exchanged with hydrogen ions; or (b) the zeolite exchanged with a metallic ion or metallic oxide other than alkali metals and/or impregnated with a metallic oxide. A more recent patent document, U.S. Pat. No. 4,822,943 (Burress), teaches a process for the selective propylation of cumene with the selective production of meta-diisopropylbenzene and para-diisopropylbenzene by contacting mixtures of cumene and propylene with a ZSM-12 catalyst under sufficient propylation conditions.

U.S. Pat. Nos. 5,004,841 and 5,175,135 (Lee) teach processes for producing mixtures of substituted aromatic compounds enriched in the linear alkylated isomers, such as para-diisopropylbenzene, by alkylating benzene with an alkylating agent, such as propylene, in the presence of an acidic mordenite zeolite catalyst. A recent PCT published application, WO0226671 (Chen), teaches a process for preparing a mixed dialkylbenzene product, such as diisopropylbenzenes, in which a predominant proportion above 60 wt % of the meta-dialkylbenzene isomer and a correspondingly low proportion of the ortho-dialkylbenzene isomer, is produced by a liquid-phase alkylation of a suitable olefin and aromatic feed utilizing an alkylation catalyst selected for enhancement of meta-isomer formation followed by or carried out in combination with a meta-isomer enhancement utilizing a catalyst selected for enhancement of meta-isomer formation.

Since late 1980s, alkylation of benzene with ethylene and propylene for the production of ethylbenzene and cumene over zeolite catalysts under liquid phase or partial liquid phase conditions has been gaining favor among the producers of these alkyl aromatic compounds due to the higher product purity and higher product yield achieved by these technologies compared with older competing technologies. These liquid phase zeolite-based alkylation technologies, in particular, have supplanted the older and less efficient aluminum chloride and solid phosphoric acid based technologies due their higher product quality and lower capital and operating costs. These zeolite-based technologies also provided additional advantages over the older technologies in that they are non-corrosive and environmentally benign.

The liquid phase and partial liquid phase zeolite-based alkyl aromatic processes typically include a reaction section that comprises: (a) an alkylation zone wherein feed aromatic and olefin react to the desired alkyl aromatic product, some recoverable (usable) byproducts and some unrecoverable (unusable) byproducts; (b) a transalkylation zone wherein recovered recoverable byproducts react with feed aromatic to form additional desired alkyl aromatic product and (c) a separation section to isolate and recover the desired alkyl aromatic product, recover and recycle unconverted feed aromatics and recoverable byproducts, and isolate and purge the unrecoverable byproducts. Alternatively, the reaction section may comprise a combined (integrated) alkylation/transalkylation zone.

In the above-described liquid phase or partial liquid phase alkyl aromatic alkylation technologies, it is typical to operate the alkylation reactors at temperatures between about 150° F. (66° C.) and 900° F. (482° C.) and at an overall aromatic to olefin molar ratio typically in a range between about 1:1 and 10:1 to control the proportion of byproducts produced together with the desired alkyl aromatic compounds. The overall olefin feed weight hourly space velocity for such processes typically is in the range of between about 0.05 and 20 $hr^{-1}$.

The liquid phase transalkylation reaction takes place over suitable zeolite transalkylation catalyst(s) at temperatures between about 150° F. (66° C.) and 900° F. (482° C.) and at an overall aromatic to byproduct weight ratio typically in a range between about 0.2:1 and 20:1 to control the proportion of byproducts produced together with the desired alkyl aromatic compounds. The overall transalkylator feed weight hourly space velocity typically is in the range of between about 0.1 and 20 $hr^{-1}$.

With an integrated alkylation/transalkylation zone, the combined alkylation/transalkylation zone typically is operated at temperatures between about 150° F. (66° C.) and 900° F. (482° C.) and at an overall feed aromatic to olefin molar ratio in the range between about 1:1 and 10:1 to control the proportion of byproducts produced together with the desired alkyl aromatic compounds, and with an overall olefin feed weight hourly space velocity in a range of between about 0.05 $hr^{-1}$ and 20 $hr^{-1}$. The overall feed aromatic to byproduct weight ratio preferentially is kept in a range between about 0.2:1 and 20:1 to control the amount of byproducts produced together with the desired alkyl aromatic compounds. The combined alkylation/transalkylation process can be operated in either the liquid phase or partial liquid phase.

Although a number of different zeolite catalysts can be used in the production of alkyl aromatic compounds, such as ethylbenzene and cumene in liquid phase or partial liquid phase, as described above, some of the zeolite catalysts that might be employed in such processes also promote oligomerization of the olefins in the feed. Some of the heavier olefin oligomers that may be formed over these zeolite catalysts can accumulate on the catalyst over time and cause catalyst activity to decline gradually over time. The gradual decline in alkylation catalyst activity, if not recovered in time, eventually can render the catalyst useless for further production of desired alkyl aromatic compounds, either because of a decline in feedstock conversion or a decline in product yield, selectivity and/or purity. The catalyst employed then would need to be regenerated or reactivated before it can be used again for further production of the desired alkyl aromatic compounds, or else it might be discarded and replaced with fresh catalyst.

Due to the relatively high concentration of olefin in the aromatic alkylation reactor, typically about 1 percent by weight or higher, and the low temperatures employed in a liquid phase or partial liquid phase aromatic alkylation reaction, formation of olefin oligomers over the zeolite catalyst utilized for the alkylation reaction and the accumulation of such oligomers on the zeolite catalyst can lead to rapid deactivation of some zeolite catalysts thereby severely limiting the run length of those catalysts before regeneration or reactivation is required. One major reason why the build-up of oligomers on the zeolite catalyst and the resulting gradual degradation of catalyst activity become particularly serious in liquid phase or partial liquid phase operations is that the low alkylation reaction temperatures employed in such operations do not promote efficient continuous removal of oligomers from the surface of the zeolite catalyst, such as by cracking of the oligomers to lighter hydrocarbon compounds and/or by desorption and/or diffusion of the oligomers and their fragments.

Furthermore, the low reaction temperatures employed in modem liquid phase or partial liquid phase alkylation, transalkylation and combined alkylation/transalkylation operations allow substantial basic material, polar compounds and nitrogen-containing contaminants in the feedstocks to adsorb and accumulate on the active sites of the zeolite catalyst thereby blocking access of the aromatic and olefin reactants the active sites and thus reducing the catalyst activity gradually over time. The long term accumulation of such basic material, polar compounds and/or nitrogen-containing contaminants from the feedstocks significantly reduces the number of active sites available to the reactants and thus lowers catalyst activity to such an extent that the catalyst is rendered substantially useless for the production of desired alkyl aromatic compounds, either because of a decline in feedstock conversion or because of a deterioration in product yield, selectivity and/or purity. The catalyst employed then would need to be regenerated or reactivated before it can be used again for further production of the desired alkyl aromatic compounds, or else it must be discarded and replaced with fresh catalyst.

Catalyst deactivated by accumulation of oligomers on the catalyst can sometimes at least partially be regenerated or reactivated by removing these heavier oligomers by hydrogen stripping of the spent catalyst at elevated temperatures, thus partially hydrogenating and cracking the oligomers on the spent catalyst into light hydrocarbons that desorb from the catalyst and are carried away by the stripping gas. Due to the high temperatures required to perform such a hydrogen stripping procedure, at least some of the basic material, polar compounds and nitrogen-containing contaminants that also have accumulated on the catalyst and occupied active sites during normal use, thereby causing additional catalyst deactivation, may also be cracked and/or desorbed.

Another approach to reactivating the catalyst deactivated by accumulation of oligomers is by stripping the spent catalyst with substantially inert hydrocarbons different from the feedstocks. Yet another approach to regenerating or reactivating catalyst deactivated by accumulation of oligomers is to conduct a controlled "air burn" in an effort to oxidize all of the carbonaceous materials, including the oligomers, deposited on the spent catalyst to form carbon monoxide, carbon dioxide and water, which desorb rapidly from the catalyst and are carried away by the regeneration gas. Similar to the hydrocarbon stripping approach discussed above, due to the high temperatures employed during an "air burn" process, much of the basic material, polar compounds and nitrogen-containing contaminants that have become adsorbed on the catalyst during normal use and occupy active sites thereby deactivating the catalyst, also may be desorbed.

Among the three procedures mentioned above, the controlled air-bum usually is considered to be the most effective way of recovering catalyst activity. Not only substantially all of the oligomeric (polymeric) compounds, basic material, polar compounds and nitrogen-containing contaminants can be removed by such a procedure, the catalyst activity usually is expected to be substantially fully recovered as essentially all of the carbonaceous material deposited on the catalyst that may block the access of reactants to active sites also are removed. The procedure of controlled air burn thus is considered the conventional way to achieve the goal of catalyst regeneration. The controlled air-bum process can be carried out either in-situ, if the reaction vessel is designed to allow operation under regeneration conditions, or ex-situ, in which the catalyst is removed from the reaction vessel and regenerated in a separate designated vessel. However, this catalyst regeneration approach may be limited by concerns about the catalyst losing its structural integrity, for example, due to de-alumination of the spent zeolite catalyst when it is being treated at high temperature by the steam that is generated during the oxidation of the carbonaceous material deposited on the catalyst during air bum, and/or losing the desired product selectivity during the severe conditions during a controlled air burn.

In addition, the procedures of catalyst reactivation by controlled air burn and stripping at elevated temperatures with hydrogen or substantially inert hydrocarbons involve significant numbers of steps and significant changes in the operation conditions of the alkylation and/or transalkylation reactor. Such added steps typically include draining or purging the reactor to substantially remove all or most of the process hydrocarbons therein, including the aromatic compounds; heating up the reactor to the desired elevated temperatures under an inert material, like nitrogen; introducing the stripping hydrocarbon required in the hydrocarbon stripping, the hydrogen gas required in the hydrogen stripping procedure or the oxygen required in the "air burn" procedure in a controlled manner to facilitate controlled removal of oligomers and other contaminants; subsequently and substantially freeing the reactor of the stripping hydrocarbon, hydrogen or oxygen with an additional purge using inert material, like nitrogen; and finally, cooling the reactor down to reaction temperature prior to re-introduction of aromatic and olefin feedstocks for the resumption of the production of the desired alkyl aromatic compounds. These elaborate reactivation procedures thus can consume a large quantity of material and utility and take a significant amount of time, thus resulting in substantial material, utility and labor costs and a significant loss of production while the reactor is off-line.

Some attempts have been made in this art to reduce and/or minimize the undesirable high material, utility and labor costs, the loss in production due to long and elaborate catalyst reactivation procedures and/or the potentially negative effects on the catalyst associated with conventional air burn catalyst regeneration. For example, U.S. Pat. No. 3,851,004 (Yang) teaches an alkylation process in which an alkylatable organic compound is contacted and reacted with an alkylation agent in a catalytic conversion zone containing a catalyst composition comprising at least one hydrogenation agent of the group of nickel, platinum, palladium, ruthenium and rhodium and a three-dimensional crystalline zeolite molecular sieve having a pore diameter large enough to adsorb ortho-diethylbenzene, an alkali metal content of less than 3.5 weight percent on a solid basis, and an $SiO_2/Al_2O_3$ molar ratio of at least 2.0, wherein the contact and reaction are continued until the alkylation activity of the catalyst has decreased. This patent teaches periodically contacting and hydrogenating the spent catalyst composition at a temperature of from 80° F. to 572° F., with a liquid solution of hydrogen in a saturated hydrocarbon having from 4 to 12 carbon atoms, the solution containing at least 0.1 mole percent dissolved hydrogen, until the alkylation activity of the catalyst is improved.

U.S. Pat. No. 4,049,739 (Zabransky) teaches a continuous fixed bed catalytic alkylation and catalyst reactivation process using a simulated moving catalyst bed to effect simultaneously in different zones of a multi-zone, fixed catalyst bed, an alkylation and a reactivation of catalyst wherein the reaction is carried out over a crystalline aluminosilicate zeolite catalyst composited with a Group VIII metal hydrogenation agent and in which the catalyst reactivation medium utilized includes alkylatable aromatic hydrocarbon and hydrogen.

U.S. Pat. No. 4,857,666 (Barger) teaches an alkylation-transalkylation process for the production of a monoalkylated aromatic compound that is said to maximize the production of desirable monoalkylaromatic compounds, while limiting transalkylation catalyst deactivation. The process includes the combination of an alkylation reactions zone, a first separation zone, a second separation zone and a transalkylation reaction zone wherein the alkylation catalyst and transalkylation catalyst are dissimilar and where the alkylation catalyst is comprised of phosphoric acid material and the transalkylation catalyst is comprised of a crystalline aluminosilicate material. Transalkylation catalyst deactivation is reduced in this process by transalkylating only dialkylated aromatic compounds. Additionally, the transalkylation catalyst is said to be regenerable utilizing a hot liquid aromatics wash.

U.S. Pat. No. 4,908,341 (Pruden) teaches a method for regenerating a spent porous crystalline catalyst, optionally associated with a metal component, such as noble and/or base metal(s). The method comprises contacting the spent catalyst, which has become deactivated by accumulation of carbonaceous residue during dewaxing, with one or more light aromatic compounds at a temperature between 700° F. and 1200° F. under conditions resulting in reactivation of the catalyst. The light aromatic compounds employed in this process have a boiling point not higher than about 220° C. and also have the capability of penetrating the catalyst so as to contact the carbonaceous residue contained therein, thereby undergoing alkylation by alkyl fragments contributed by components of the carbonaceous residue and thereafter diffusing from or otherwise escaping from the catalyst.

U.S. Pat. No. 5,012,021 (Vors) teaches a process for the production of alkylaromatic hydrocarbons wherein a $C_6$-$C_{22}$ paraffinic hydrocarbon feed is dehydrogenated, selectively hydrogenated and stripped to remove substantially all $C_6$-$C_{22}$ diolefins and $C_6$ minus light hydrocarbon, resulting in a liquid stream comprising $C_6$-$C_{22}$ paraffinic hydrocarbons and $C_6$-$C_{22}$ monoolefinic hydrocarbons which is reacted with an aromatic hydrocarbon stream to produce the desired alkylaromatic compounds in an alkylation zone containing solid alkylation catalyst. It was taught that one of the by-products of the alkylation reaction is the formation of gum-type polymers that accumulate on the surface of the catalyst and block reaction sites. The preferred alkylation reactor arrangement suggested consists of two parallel reactors that alternately receive feed and a hot benzene wash so that one reactor is making product while the other undergoes regeneration. In addition to benzene washing, other regeneration techniques may include a carbon burning step for certain catalysts such as inorganic acids, zeolite or alumina-silica.

U.S. Pat. No. 5,118,897 (Khonsari) teaches a process for reactivating alkylation catalyst that comprises contacting alkylation catalyst with hydrogen and benzene in the substantial absence of olefin. The reactivation process may be conducted under conditions (e.g., temperature, pressure) similar to those employed in an alkylation reaction. This process further describes reactivating the catalyst in situ over a relatively short time, thus minimizing disruption of the alkylation operation.

U.S. Pat. No. 5,146,026 (Tejero) teaches a continuous process for alkylating aromatic hydrocarbons in a fixed bed catalytic reactor in liquid phase over an alkylation catalyst comprising at least one selected from the group consisting of natural zeolites, synthetic zeolites and clay, at least one being of aluminum silicate and magnesium silicate. The process further comprises periodically regenerating the catalyst by contacting spent catalyst with a stream of at least one paraffin alternating with a stream of at least one alcohol, in cycles lasting for a period of time within the range of about 2 to 8 hours at a temperature within the range of about 150° C. to 300° C. and at a liquid hourly space velocity of 1 to 10 $hr^{-1}$.

European Patent No. EP 0 353 813 (Tejero) teaches a continuous process for alkylating aromatic hydrocarbons in a fixed bed catalytic reactor in liquid phase. The solid catalysts used for the desired alkylation of benzene with $C_{10}$-$C_{14}$ detergent range paraffin mono olefins to give linear monoalkyl-benzenes of the same detergent range with high yield, purity and selectivity are zeolites and/or clays having a basic composition of aluminum and/or magnesium silicate. The process further comprises regenerating the catalyst semi-continuously and cyclically by means of passing into contact with the catalyst alternating and successive streams of paraffins and other products of different polarity, thus obtaining a long-lasting catalytic effectiveness.

U.S. Pat. Nos. 5,212,128 and 5,306,681 (Schorffieide) teach a process for recovering the isomerization activity of hydroisomerization catalyst comprising Group VI and/or Group VIII metal on halogenated refractory metal oxide by subjecting the catalyst to a wash using light aromatic solvents at elevated temperature, e.g., toluene at 300° C. In these processes, the hot aromatic solvent wash may be preceded by a hot hydrogen-containing gas strip. Catalyst activity can be maintained by the continuous or periodic addition of light aromatic solvent or light aromatic-containing materials to the feeds sent to the isomerization catalyst.

A process for at least partially reactivating deactivated aromatic alkylation catalyst in situ by contacting it with at least one polar compound in liquid phase is taught in U.S. Pat. No. 6,525,234 (Dandekar). The process comprises the steps of: (a) contacting a feed containing alkylatable aromatic, such as benzene, under liquid phase alkylation conditions with an alkylating agent, such as ethylene, in the presence of alkylation catalyst comprising a porous crystalline material, such as MCM-22, to provide an alkylated aromatic product during which contacting the catalyst becomes at least partially deactivated by absorbing catalyst poisons present in the feed; (b) treating the at least partially deactivated catalyst in situ by contacting it with at least one polar compound, such as water or acetic acid, having a dipole moment of at least 0.05 Debyes under conditions of temperature and pressure employed in the liquid phase alkylation that are sufficient to at least partially desorb the catalyst poison from the catalyst; and (c) collecting the alkylated aromatic product.

PCT published application WO0183408 (Dandekar) teaches a process for alkylating an alkylatable aromatic compound in which the process includes: (a) contacting the alkylatable aromatic compound and an alkylating agent with an alkylation catalyst under alkylation conditions; and (b) when the alkylation catalyst has become at least partially deactivated, contacting the alkylation catalyst with a $C_1$-$C_8$ hydrocarbon under alkylation catalyst reactivation conditions. The process is said to provide rejuvenation of catalyst activity comparable to air regeneration.

A process for regenerating a spent aromatic alkylation or transalkylation catalyst comprising a molecular sieve by contacting the spent catalyst with an oxygen-containing gas at a temperature of about 120 to about 600° C. and then contacting the catalyst with an aqueous medium, such as an ammonium nitrate solution, an ammonium carbonate solution or an acetic acid solution, is taught in published PCT application WO03/006160 (Dandekar).

The foregoing prior art processes for reactivation of catalysts, however, either only apply to catalysts used in reactions other than liquid phase or partial liquid phase alkylation and/or transalkylation over zeolite catalysts for the production of alkyl aromatic compounds, or else they involve contacting the deactivated catalyst with material that is not required, used or produced in the aromatic alkylation reaction. These prior art processes, therefore, either do not apply directly to the need for an efficient and effective technique for reactivating the deactivated catalyst employed in a process for production of alkyl aromatic compounds using liquid phase or partial liquid phase alkylation and/or transalkylation over zeolite catalyst, or they are not economical in such applications.

An efficient way to substantially recover the activity of the deactivated zeolite alkylation catalyst used in production of alkyl aromatic compounds by liquid phase or partial liquid phase alkylation reaction of aromatics and olefin therefore still is needed. Preferably, the reactivation process should not require any material that is foreign to the alkylation process, such as nitrogen, hydrogen, oxygen, air, natural gas, steam, water or hydrocarbons that normally are not required, used or produced in the alkylation reaction. A reactivation process that involves materials foreign to the alkylation process may incur additional costs due to the loss or all or part of these materials and/or the material normally required, used or produced in the process. Further, such foreign materials may incur additional capital and operating costs due to additional equipment, utilit and labor required to separate and/or recover the foreign materials and/or the material normally required, used or produced in the process. The additional equipment required may include the need for one or more storage tanks for the stripping gas or stripping hydrocarbons, a compressor for the stripping gas, a pump for the stripping hydrocarbons, heat exchangers to bring the material used solely for the reactivation procedure to the desired temperature, apparatus to separate and recover the stripping materials and/or those normally required, used or produced in the alkylation reactor, their ancillary apparatuses and equipment required for disposal of contaminated materials.

Also preferably, a catalyst reactivation procedure adapted for use in alklation processes should not require steps that must be carried out at temperatures so much higher than the normal alkylation temperatures that an upgrade in the reactor's material of construction would be required to allow for the reactivation procedure. In addition, the reactivation procedure should be as simple as possible and preferably include as few steps as possible and involve as few changes in operating conditions (such as reactor temperature) as possible to reduce the complexity and cost of the operation and to minimize the possibility of operational mistake. Also, preferaly the reactivation procedure should be carried out in-situ and its operation limited to the reaction section, while the other parts of the alkyl aromatic plant (e.g. other reactors and the distillation, separation and/or purification sections) can be operated either substantially as normal or idled. The limitations and deficiencies of the prior art techniques are overcome in whole or at least in part by the improved processes of this invention.

OBJECTS OF THE INVENTION

Accordingly, a general object of this invention is to provide improved alkylation processes, which herein is meant broadly to include processes to produce alkyl aromatic compounds by means of an alkylation reaction, which may be carried out in combination with other reactions, such as transalkylation and/or isomerization to convert recoverable byproducts produced from the alkylation reaction to the desired product and/or to intermediate products, for production of alkyl aromatic compounds over zeolite catalyst(s) together with improved integrated methods for recovering the activity of at least partially deactivated zeolite catalyst(s) used in the processes thereby minimizing additional capital and operating costs associated with reactivation procedures.

Another general object of this invention is to provide improved methods for recovering the activity of at least partially deactivated zeolite catalyst(s) used in liquid phase or partial liquid phase reactions in an alkylation process for production of alkyl aromatic compounds by utilizing catalyst activating stream(s) comprising only materials that are required, used or produced during normal operation of the alkylation processes for production of alkyl aromatic compounds from aromatics and olefins.

Yet another general object of this invention is to provide improved methods for reactivating at least partially deactivated zeolite catalyst(s) utilized in a process for production of alkyl aromatic compounds wherein alkylation and transalkylation and/or isomerization reactions are carried out in liquid phase or partial liquid phase over zeolite catalyst(s) wherein the improved methods employ fewer steps and/or changes in the reactor operating conditions (such as temperature, pressure or chemical composition) than required for practicing prior art processes in order to reduce the complexity and/or cost of the catalyst reactivation procedure and/or minimize the possibility of operational mistake.

A principal object of this invention is to provide alkylation processes for production of alkyl aromatic compounds over zeolite catalyst(s) under liquid phase or partial liquid phase operating conditions from feed aromatics and olefin compounds in combination with improved methods for partly or substantially recovering the activity of at least partially deactivated zeolite catalyst(s) used in alkylation processes, following deactivation of the zeolite catalyst(s) due to accumulation of the catalyst(s) of at least one material selected from the group consisting of oligomeric (polymeric) compounds, basic material, polar compounds and nitrogen-containing contaminants.

A specific object of this invention is to provide improved alkylation processes for production of alkyl aromatic compounds over zeolite catalyst(s) under liquid phase or partial liquid phase operating conditions from feed aromatics and olefin compounds in combination with improved methods for partly or substantially recovering the activity of at least partially deactivated zeolite catalyst(s) used in alkylation processes following deactivation of the zeolite catalyst(s) primarily due to accumulation of oligomeric (or polymeric) material on the catalyst(s).

Another specific object of this invention is to provide improved alkylation processes for production of alkyl aromatic compounds over zeolite catalyst(s) under liquid phase or partial liquid phase operating conditions from feed aromatics and olefin compounds in combination with improved methods for partly or substantially recovering the activity of at least partially deactivated zeolite catalyst(s) used in alkylation processes deactivation of the zeolite catalyst(s) primarily due to accumulation on the catalyst(s) of at least one material selected from the group consisting of basic material, polar compounds, and nitrogen-containing contaminants.

Other objects and advantages of the present invention will in part be obvious and will in part appear hereinafter. The invention accordingly comprises, but is not limited to, the processes and methods and related apparatus, involving the several steps and the various components, and the relation and order of one or more such steps and components with respect to each of the others, as exemplified by the following description. Various modifications of and variations on the methods and apparatus as herein described will be apparent to those skilled in the art, and all such modifications and variations are considered within the scope of the invention.

SUMMARY OF THE INVENTION

Improved, integrated processes and methods are provided for the production of alkyl aromatic compounds over zeolite catalyst(s) and for the reactivation of at least partially deactivated zeolite catalyst(s) employed in such processes. The zeolite-based alkylation processes include a reaction section where the feed aromatic and olefin are reacted to the desired alkyl aromatic compounds, some recoverable byproducts, and some other unrecoverable byproducts, and a separation section to isolate and recover the desired alkyl aromatic product, recover and recycle the unconverted feedstock and recoverable byproducts, and isolate and purge the unrecoverable byproducts.

The reaction section may comprise an alkylation zone in which the feed aromatic and olefin react to the desired alkyl aromatic compounds, some recoverable byproducts, and some other unrecoverable byproducts over a zeolite alkylation catalyst, and a transalkylation zone in which the recoverable byproducts react with feed aromatic to form additional desired alkyl aromatic compounds over a zeolite transalkylation catalyst. The alkylation and the transalkylation zones in accordance with this invention may be operated in anyone of three possible modes: alkylation-transalkylation sequentially in series; transalkylation-alkylation sequentially in series; or alkylation-transalkylation carried out in parallel. For production of dialkyl aromatic compounds, such as diethylbenzenes and diisopropylbenzenes, an isomerization zone may be used in addition to or in lieu of the transalkylation zone.

Alternatively, the reaction section may comprise a combined alkylation/transalkylation and/or a combined alkylation/isomerization zone in which the feed aromatic, the feed olefin, and the recycle recoverable byproducts react to form the desired alkyl aromatic compounds, some recoverable byproducts and some other unrecoverable byproducts, over zeolite catalyst(s) suitable for both the alkylation reactions and the transalkylation reactions and/or alkylation and isomerization reactions.

The olefin feed in accordance with this invention preferably consists essentially of olefins containing less than 6 carbon atoms, such as from 2 to 5 carbon atoms, more preferably from 2 to 4 carbon atoms. More specifically, the olefin feed preferably contains at least one member selected from the group consisting of ethylene, propylene, 1-butene, cis-2-butene, trans-2-butene and isobutene. More preferably, the olefin feed consists essentially of ethylene and/or propylene. The aromatic feedstock preferably consists essentially of at least one member selected from the group consisting of benzene, toluene, ethylbenzene, xylenes, cumene, n-propyl benzene and butylbenzenes isomers. More preferably the aromatic feed is benzene. The desired alkyl aromatic compounds that may be produce in accordance with this invention include, but are not limited to, the following: ethylbenzene, cumene, n-propyl benzene, butylbenzenes, diethylbenzenes, diisopropylbenzenes, dibutylbenzenes, ethyltoluenes, cymenes, butyltoluenes, ethylcumenes, butyl ethylbenzenes, butylcumenes and mixtures thereof. Preferably, the desired alkyl aromatic compound is one selected from the group consisting of ethylbenzene, cumene, diethylbenzene isomer mixture, para-diethylbenzene, meta-diethylbenzene, diisopropylbenzene isomer mixture, para-diisopropylbenzene and meta-diisopropylbenzene and mixtures thereof.

An alkylation reaction in accordance with this invention may be carried out in liquid phase or partial liquid phase over suitable zeolite alkylation catalyst at temperatures between about 150° F. (66° C.) and 900° F. (482° C.), preferably between about 180° F. (82° C.) and 600° F. (316° C.). In the case of liquid phase alkylation, the alkylation reactor pressure is kept above a certain minimum pressure to assure that the reaction mixture remains in liquid phase throughout the alkylation reaction zone. In the case of partial liquid phase operation, the alkylation reaction pressure is established according to the reaction temperature and the predetermined optimal distribution of the reaction mixture between liquid and vapor phases.

The liquid phase and partial liquid phase alkylation reactions may be carried out at an overall aromatic to olefin molar ratio that is typically in a range between about 1:1 and 10:1 to control the proportion of byproducts produced together with the desired alkyl aromatic compounds, preferably between about 1:1 and 4:1 to minimize the amount of excess feed aromatic that needs to be recovered in the downstream separation section and recycled back to the reaction section. The overall olefin feed weight hourly space velocity is in a range of between about 0.01 and 50 hr$^{-1}$, preferably between about 0.1 and 5 hr$^{-1}$. The alkylation zone contains at least one acidic zeolite catalysts selected from the group consisting of: zeolite beta, zeolite Y, ZSM-5, ZSM-12, MCM-22, MCM-36, MCM-49, MCM-56, MCM-58, MCM-68, Faujasite, Mordenite, zirconium phosphate, porous crystalline magnesium silicates and mixtures thereof. The alkylation zone can be housed in one or more alkylation vessels. Each alkylation vessel can have one or more catalyst beds containing the same or different alkylation catalysts or catalyst mixtures. Part of the total effluent from the alkylation zone may be recycled back to some or all of the alkylation beds, with or without cooling, for purposes of controlling the reactor temperature and/or reactant composition.

The liquid phase transalkylation reaction in accordance with this invention may be carried out over suitable zeolite transalkylation catalyst(s) at temperatures between about 150° F. (66° C.) and 900° F. (482° C.), preferably between about 180° F. (82° C.) and 600° F. (316° C.). The overall transalkylator feed weight hourly space velocity is typically in a range of between about 0.02 and 100 hr$^{-1}$, preferably between about 0.2 and 10 hr$^{-1}$. The transalkylation reactor pressure is kept above a certain minimum pressure to assure that the reaction mixture remains in liquid phase throughout the transalkylation reaction zone. The liquid phase transalkylation reaction may be carried out at an overall aromatic to byproduct weight ratio that is typically in a range between about 0.1:1 and 50:1 to control the proportion of byproducts produced together with the desired alkyl aromatic compounds, preferably between about 0.2:1 and 5:1 to minimize the amount of excess feed aromatic that need to be recovered in the downstream separation section and recycled back to the reaction section. The transalkylation zone contains one or more acidic zeolite catalysts selected from the group consisting of: zeolite beta, zeolite Y, ZSM-5, ZSM-12, MCM-22, MCM-36, MCM-49, MCM-56, MCM-58, MCM-68, Faujasite, Mordenite, zirconium phosphate, porous crystalline magnesium silicates and mixtures thereof. The transalkylation zone can be housed in one or more transalkylation vessels. Each transalkylation vessel can have one or more catalyst beds containing the same or different transalkylation catalysts or catalyst mixtures.

The liquid phase isomerization reaction, if applicable, in accordance with this invention may be carried out over suitable zeolite isomerization catalyst(s) at temperatures between about 150° F. (66° C.) and 900° F. (482° C.), preferably between about 180° F. (82° C.) and 600° F. (316° C.). The overall isomerization reactor feed weight hourly space velocity is typically in a range of between about 0.02 and 100 hr$^{-1}$, preferably between about 0.2 and 10 hr$^{-1}$. The isomerization reactor pressure is kept above a certain minimum pressure to assure that the reaction mixture remains in liquid phase throughout the isomerization reaction zone. The liquid phase isomerization reaction may be carried out at an overall aromatic to byproduct weight ratio that is typically in a range between about 0.1:1 and 50:1 to control the proportion of byproducts produced together with the desired alkyl aromatic compounds, preferably between about 0.2:1 and 5:1 to minimize the amount of excess feed aromatic that needs to be recovered in the downstream separation section and recycled back to the reaction section. The isomerization zone contains one or more acidic zeolite catalysts selected from the group consisting of: zeolite beta, zeolite Y, ZSM-5, ZSM-12, MCM-22, MCM-36, MCM-49, MCM-56, MCM-58, MCM-68, Faujasite, Mordenite, zirconium phosphate, and porous crystalline magnesium silicates. The isomerization zone can be housed in one or more isomerization vessels. Each isomerization vessel can have one or more catalyst beds containing the same or different isomerization catalysts or catalyst mixtures.

The combined alkylation/transalkylation and/or alkylation/isomerization zone in accordance with this invention may be operated at temperatures between about 150° F. (66° C.) and 900° F. (482° C.), preferably between about 180° F. (82° C.) and 600° F. (316° C.) and at an overall feed aromatic to olefin molar ratio in a range between about 1:1 and 10:1 to control the proportion of byproducts produced together with the desired alkyl aromatic compounds, preferably between about 1:1 and 4:1 to minimize the amount of excess feed aromatic that needs to be recovered in the downstream separation section and recycled back to the reaction section. The overall olefin feed weight hourly space velocity may range between about 0.01 hr$^{-1}$ and 50 hr$^{-1}$, preferably between about 0.1 hr$^{-1}$ and 5 hr$^{-1}$. The overall feed aromatic to byproduct weight ratio may be in a range between about 0.1:1 and 50:1 to control the proportion of byproducts produced together with the desired alkyl aromatic compounds, preferably between about 0.2:1 and 5:1 to minimize the amount of excess feed aromatic that needs to be recovered in the separation section and recycled back to the reaction section.

The combined alkylation/transalkylation zone can be operated in liquid phase or partial liquid phase and contains one or more acidic zeolite catalysts selected from the group consisting of: zeolite beta, zeolite Y, ZSM-5, ZSM-12, MCM-22, MCM-36, MCM-49, MCM-56, MCM-58, MCM-68, Faujasite, Mordenite, zirconium phosphate, porous crystalline magnesium silicates and mixtures thereof. In the case of liquid phase operation, the reaction pressure is kept above a certain minimum pressure to assure that the reaction mixture remains in liquid phase throughout the reaction zone. In the case of partial liquid phase operation, the reaction pressure is established according to the reaction temperature and the predetermined optimal distribution of the reaction mixture between liquid and vapor phases. The combined alkylation/transalkylation zone can be housed in one or more alkylation/transalkylation vessels. Each alkylation/transalkylation vessel can have one or more catalyst beds containing the same or different catalysts or catalyst mixtures. Part of the total effluent from the combined alkylation/transalkylation zone may be recycled back to some or all of the alkylation/transalkylation beds, with or without cooling, for purposes of controlling the reactor temperature and/or reactant composition.

The combined alkylation/isomerization zone can be operated in liquid phase or partial liquid phase and contains one or more acidic zeolite catalysts selected from the group consisting of: zeolite beta, zeolite Y, ZSM-5, ZSM-12, MCM-22, MCM-36, MCM-49, MCM-56, MCM-58, MCM-68, Faujasite, Mordenite, zirconium phosphate, and porous crystalline magnesium silicates. In the case of liquid phase operation, the reaction pressure is kept above a certain minimum pressure to assure that the reaction mixture remains in liquid phase throughout the reaction zone. In the case of partial liquid phase operation, the reaction pressure is established according to the reaction temperature and the predetermined optimal distribution of the reaction mixture between liquid and vapor phases. The combined alkylation/isomerization zone can be housed in one or more alkylation/isomerization vessels. Each alkylation/isomerization vessel can have one or more catalyst beds containing the same or different catalysts or catalyst mixtures. Part of the total effluent from the combined alkylation/isomerization zone may be recycled back to some or all of the alkylation/isomerization beds, with or without cooling, for purposes of controlling the reactor temperature and/or reactant composition.

Integrated methods in accordance with this invention for reactivating at least partially deactivated zeolite catalyst(s) employed in a reaction zone comprise at least the following sequential procedures:

(a) stop or substantially reduce the normal charge(s) to the reaction zone; introduce a catalyst reactivating agent, preferably aromatic stripping stream consisting essentially of at least one member selected from the group consisting of the feed aromatic compound, the desired alkyl aromatic product, and certain byproducts made in the process, at a weight hourly space velocity between about 0.02 $hr^{-1}$ and 200 $hr^{-1}$, preferably between about 0.2 $hr^{-1}$ and 50 $hr^{-1}$; raise the reaction zone temperature to an elevated temperature above the normal reaction zone operating temperature by about 10° C. to 200° C., preferably by about 20° C. to 140° C.;

(b) allow the at least partially deactivated catalyst(s) to be substantially or at least partially reactivated while maintaining the elevated reaction zone temperature over a period of time between about 1 hour and 30 days, preferably between about 6 hours and 7 days, or more preferably between about 12 hours and 4 days, while maintaining the operation of the rest of the plant at substantially the same conditions as during normal operation or idling the operation of at least part of the plant; removing catalyst contaminants and deactivating materials, such as stripped oligomers, their fragments and/or derivatives, and/or other contaminants, their fragments and/or derivatives by distillation in existing apparatus, by purging, and/or by selective adsorption with a suitable adsorbent;

(c) terminate the flow of the aromatic stripping stream at the conclusion of the reactivation procedure, re-establish the normal reaction zone operating conditions and the normal reaction zone charge(s), and resume normal production of the desired alkyl aromatic compounds.

Because the integrated catalyst reactivation methods of the present invention do not utilize material foreign to the process, no additional equipment is required to transfer, store and charge the catalyst reactivating/stripping agent to the process. Also, no additional apparatus is required to separate and/or recover the reactivating/stripping agent other than those normally required, used, or produced in the process. In addition, because no foreign stripping gas, such as hydrogen, nitrogen, air, or oxygen, is used in this invention, apparatus typically required for circulating the stripping gas in order to minimize the cost of stripping material, such as a gas cooler, condenser, gas-liquid separator, compressor or gas heater are not required.

The oligomers, basic material, polar compounds, nitrogen-containing contaminants, and/or the fragments and/or derivatives of the aforementioned compounds removed from the at least partially deactivated catalyst during catalyst reactivation can be substantially removed from the stripping stream by distillation in existing apparatus, by purging, and/or by selective adsorption with suitable adsorbent. Some of the oligomers, their fragments; and some other heavier contaminants that desorbed from the catalyst during the catalyst reactivation procedure may be easily removed from the stripping stream as heavies purge(s) at or near the bottom of existing distillation column(s). Some of these heavier contaminants may enter the process with the fresh feedstocks or may be formed on the catalyst by reaction of their precursor contaminants in the feedstocks with the feed olefin compounds and/or the aromatic compounds present on the catalyst. Some lighter fragments of the oligomers and lighter contaminants may be easily separated from the stripping stream in existing distillation column(s) and removed in light end purge(s) at or near the top of existing distillation column(s). Some of these lighter contaminants may enter the process with the feedstocks or may be formed by cracking of heavier contaminants present on the catalyst.

For removal of desorbed contaminants from the stripping stream by selective adsorption, suitable adsorbent applicable to this invention include at least one member selected from the group consisting of: acidic clay, zeolites, zeolite catalysts, molecular sieves, silicates, aluminas, activated aluminas, activated carbon, silica gel, and ion exchange resins. Because the adsorbent is only needed during reactivation of at least partially deactivated catalyst, used adsorbent can be regenerated conveniently, when needed, while the plant is operated normally and the adsorbent is not used. The spent (used) adsorbents can be regenerated by removing the adsorbed contaminants under favorable conditions. Regeneration of the spent adsorbent can be accomplished, according to this invention, by subjecting the adsorbent under elevated temperatures to a flow of an inert gas (i.e., inert relative to the adsorbent and the adsorbed contaminants) such as nitrogen, air, natural gas, liquefied petroleum gas, methane, ethane, propane, or steam, or to a flow of an inert liquid such as n-pentane, cyclopentane, n-hexane, cyclohexane, benzene, toluene, or xylenes. Some adsorbents can alternatively be regenerated by displacing the adsorbed contaminants by other compound(s), which is (are) preferentially adsorbed on the adsorbent more strongly than the contaminants. Since water is typically very strongly adsorbed on most of the aforementioned adsorbents, water or mixtures containing a high level of water can typically be used to effectively remove the contaminants from the adsorbents. Some adsorbents may also be regenerated by acid treatments such as by washing them with a stream of acidic mixtures.

Because the regeneration of spent adsorbent, if required, can be carried out conveniently and during periods when the plant is operated normally, this procedure does not affect the production of the desired alkyl aromatic compounds. Furthermore, the quantity of selective adsorbent required is much less than the amount of catalyst being used, and the regeneration of spent adsorbent typically requires less severe operating conditions than catalyst reactivation by conventional techniques such as hydrogen stripping or air burn, in particular lower temperature. Due to the relatively small quantity of adsorbent required, the adsorbent regeneration gas, if needed, can be used on a once-through basis to minimize capital costs. The total cost associated with regenerating the spent adsorbent is therefore much lower than the costs associated with reactivating deactivated catalyst by conventional hydrogen stripping or air burn.

DESCRIPTION OF PREFERRED EMBODIMENTS

The following examples are provided for illustrative purposes only and should not be construed to limit the appended claims in any manner whatever.

EXAMPLE 1

A batch of 24 grams of MCM-22 type catalyst was loaded into a pilot plant alkylation reactor and tested for cumene synthesis. Between the catalyst on-stream hours of 4,698 and 4,770, the benzene charge was about 168 grams per hour, and the propylene charge was about 23 grams per hour. The reactor inlet temperature was about 148° C., and the propylene conversion had dropped to about 97.2%. The reactor pressure was maintained at above 320 psig to assure liquid phase operating conditions. At 4,769 hours on-stream, the propylene charge was stopped while the benzene charge was continued, and the reactor inlet temperature was raised to 167° C. The reactor inlet temperature was later raised to and maintained at 200-215° C., in accordance with the present invention, for about 20 hours before it was lowered back to about 148° C. at 4,819 hours on-stream. The propylene charge was subsequently re-introduced. At 4,838 hours on-stream, the propylene conversion was found to be about 98.7%. The improvement of propylene conversion from 97.2 to 98.7% suggested significant recovery of catalyst activity as a result of catalyst reactivation in accordance with this invention.

Thereafter, the propylene charge was again stopped while the benzene charge was continued, and the reactor inlet temperature was raised once again to 210-233° C. where it was maintained for about 20 hours. The temperature was then lowered back to 148° C., and the propylene charge was again re-introduced. At 4,910 hours on-stream, the propylene conversion was found to be about 99.2%, a further improvement above the earlier 98.7% conversion level. The overall improvement of propylene conversion from 97.2 to 99.2% indicated significant recovery of catalyst activity and demonstrated the effectiveness of what might be called a hot aromatic wash catalyst reactivation procedure in accordance with this invention.

EXAMPLE 2

A batch of 60 grams of another MCM-22 type catalyst was loaded into a pilot plant alkylation reactor and tested for cumene synthesis. Between the catalyst on-stream hours of 5,100 and 5,340, the benzene charge was about 65 grams per hour, and the propylene charge was about 30 grams per hour. The reactor inlet temperature was maintained at about 128° C., and the propylene conversion was greater than 99.999%. The reactor pressure was maintained at above 320 psig to assure liquid phase operating conditions.

At 5,341 hours on-stream, a prepared benzene feed containing 2 ppm of n-methyl pyrrolidinone (NMP) as a typical nitrogen feed contaminant was introduced through a guard bed containing a selective adsorbent, and the reactor conditions were maintained essentially the same as before. No decline in propylene conversion was detected while the contaminated benzene feed passed through the guard bed. At 5,437 hours on-stream, the guard bed was by-passed, and a slight decline in propylene conversion was noticed shortly thereafter. Clean benzene was again used shortly after this time. The propylene conversion was found to be 99.997% at 5,627 hours on-stream. At 5,631 hours on-stream, a prepared benzene feed containing 50 ppm NMP was introduced through a guard bed containing a selective adsorbent, and the reactor conditions were maintained essentially the same as before. The propylene conversion was found to be the same at 99.997% at 5,651 hours on-stream. At 5,652 hours, the guard bed was by-passed and the NMP-containing benzene feed was fed directly to the reactor, while the reactor conditions were maintained essentially the same as before. Later on, the NMP-containing benzene feed was again replaced by a pure benzene feed. At 5,747 hours on-stream, the propylene conversion was found to be less than 99.97%, indicating that the catalyst activity in the alkylation reactor had been clearly reduced by NMP poisoning.

At 5,749 hours on-stream, the propylene charge was stopped, and the benzene charge was increased to about 120 grams per hour. At the same time, the reactor inlet temperature was raised to and maintained at 240° C. in accordance with the present invention. At 5,773 hours on-stream, the reactor inlet temperature was lowered back to 128° C., and the benzene charge rate was returned to about 65 grams per hour. The propylene charge at about 30 grams per hour was then restored. At 5,795 hours on-stream, the propylene conversion was found to have increased to greater than 99.999%. The reaction conditions were kept-essentially unchanged between 5,774 and 6,155 hours on-stream, and the propylene conversion remained consistently greater than 99.999% during such period. This example demonstrated the effectiveness of a hot aromatic wash catalyst reactivation procedure in accordance with the present invention in restoring catalyst activity lost due to NMP poisoning.

EXAMPLE 3

The same pilot reactor described in Example 2 was tested for cumene synthesis. Between the catalyst on-stream hours of 5,774 and 6,156, the benzene charge was about 65 grams per hour, and the propylene charge was about 30 grams per hour. The reactor inlet temperature was maintained at about 128° C., and the propylene conversion was greater than 99.999%. The reactor pressure was maintained above 320 psig to assure liquid phase operating conditions.

At 6,157 on-stream hours, the pure benzene feed was replaced with a prepared benzene feed spiked with about 80 ppm of NMP. Later, the NMP-containing benzene feed was replaced with pure benzene feed. At 6,251 hours on-stream, the propylene conversion was found to have dropped to about 99.995%, thereby indicating deterioration of catalyst activity due to catalyst poisoning by NMP.

At 6,254 hours on-stream, the propylene charge was stopped, and the benzene charge was increased to about 120 grams per hour. At the same time, the reactor inlet temperature was raised to and maintained at about 240° C. in accordance with the present invention. At 6,284 hours on-stream, the reactor inlet temperature was lowered back to about 128° C., and the benzene charge rate returned to about 65 grams per hour. The propylene charge at about 30 grams per hour was then restored. At 6,299 hours on-stream, the propylene conversion was found to have increased to greater than 99.999%. The reaction conditions were kept essentially unchanged between 6,285 and 6,828 hours on-stream, and the propylene conversion was found consistently greater than 99.999% during such period. This example further demonstrated the effectiveness of a hot aromatic wash catalyst reactivation procedure, in accordance with the present invention, in restoring catalyst activity lost due to NMP poisoning.

The reactor effluent collected during the hot aromatic wash procedure was distilled to recover an overhead benzene fraction, which was analyzed to be of about 99.99% benzene purity and substantially free of NMP and other nitrogen compounds. The distillation column bottoms sample was found to contain about 1.3 ppm of nitrogen compounds. The recovered overhead benzene fraction was diluted with clean benzene feed at a weight ratio of 1:1.5, treated with a molecular sieve adsorbent, and fed to the reactor as benzene feed until it was substantially exhausted and the clean benzene feed re-introduced at 7,071 hours on-stream. At on-stream hours between 7,071 and 7,212 hours, the reactor conditions were maintained substantially the same as before, and propylene conversion was found to be consistently above 99.999%.

In summary, this example further demonstrated the catalyst poisoning effect of NMP contaminants in benzene feedstock in reducing the propylene conversion for production of cumene over zeolite catalyst. It also demonstrated that the catalyst activity lost due to the NMP poisoning effect can be substantially recovered by a hot aromatic wash procedure in accordance with the present invention. This example also demonstrated that the spent stripping or wash liquid can be recovered, inexpensively treated using already available distillation equipment in accordance with the present invention, and then re-used for the further production of cumene.

It will be apparent to those skilled in the art that other changes and modifications may be made in the above-described apparatus, processes and methods for carrying out alkylation processes and for periodically recovering activity of catalyst(s) lost due to accumulation on the surface of the catalyst of at least one material from the group consisting of oligomers (or polymeric compounds), basic material, polar compounds, and nitrogen-containing contaminants, without departing from the scope of the invention herein, and it is intended that all matter contained in the above description shall be interpreted in an illustrative and not a limiting sense.

All of the above-referenced patents and patent applications hereby are incorporated in their entirety by reference.

The invention claimed is:

1. A method for reactivating at least partially deactivated zeolite catalyst in one or more reaction zones in a reaction section where reactions are carried out in liquid phase or partially liquid phase for the production of alkyl aromatic compounds wherein said alkyl aromatic compounds are produced by reacting at least one feed olefin with at least one feed aromatic, said catalyst reactivation process comprising the steps of:
   (a) stopping or substantially reducing at least one selected feed to the reaction zone(s); and introducing a catalyst reactivating agent into said reaction zone(s) at a weight hourly space velocity between about 0.02 hr$^{-1}$ and 200 hr$^{-1}$; and raising the reaction zone(s) temperature(s) to temperature(s) above the normal reaction zone(s) operating temperature(s) by about 10° C. to 200° C.;
   (b) allowing said at least partially deactivated catalyst to be at least partially reactivated in said reaction zone(s) at said elevated temperature(s) over a period of time between 1 hour and 30 days;
   (c) terminating flow of said catalyst reactivating agent; and re-establishing normal reaction zone(s) operating conditions and said selected reactor charge(s); and
   (d) resuming production of said alkyl aromatic compounds in said reaction zone(s).

2. The method of claim 1 further comprising removing catalyst deactivating materials, catalyst contaminants and process contaminants by distillation, purging, selective adsorption with a suitable adsorbent or combinations thereof.

3. The method of claim 1 wherein said catalyst reactivation steps are capable of being performed while simultaneously conducting substantially all other operations in a facility for producing alkyl aromatic compounds.

4. The method of claim 1 wherein said catalyst reactivating agent comprises an aromatic stripping stream consisting essentially of at least one member selected from the group consisting of feed aromatics, alkyl aromatic products and process byproducts.

5. The method of claim 4 wherein said aromatic stripping stream is introduced at a weight hourly space velocity ranging from about 0.2 hr$^{-1}$ to about 50 hr$^{-1}$ and said temperature is raised from about 20° C. to 140° C. above said normal operating temperature and wherein said period of time is from about 6 hours to about 7 days.

6. The method of claim 1 wherein said period of time is from 12 hours to 4 days.

7. The method of claim 4 wherein said stripping stream comprises benzene.

8. The method of claim 2 wherein said catalyst contaminants comprise at least one member selected from the group consisting of oligomers and/or other heavy compounds formed from feed olefins, basic materials, polar compounds, nitrogen-containing materials and fragments and/or derivatives of the aforementioned compounds.

9. The method of claim 8 wherein heavier contaminants are purged at a bottom portion of a distillation column and wherein lighter contaminants and oligomer fragments are separated from said reactivating agent in one or more distillation columns and are removed therefrom in light end purges at a top portion of said distillation columns.

10. The method of claim 8 wherein desorbed contaminants are removed from said reactivating agent by selective adsorption by a suitable adsorbent comprising at least one member selected from the group consisting of acidic clay, zeolites, zeolite catalysts, molecular sieves, silicates, aluminas, activated aluminas, activated carbon, silica gel and ion exchange resins.

11. The method of claim 10 further comprising regenerating a spent adsorbent component, wherein said regeneration is capable of being carried out while simultaneously conducting substantially all other operations in a facility for producing alkyl aromatic compounds.

12. The method of claim 11 wherein said adsorbent regeneration further comprises subjecting said adsorbent, under elevated temperatures, to a flow of inert material comprising at least one member selected from the group consisting of nitrogen, air, natural gas, liquefied petroleum gas, methane, ethane, propane, steam, n-pentane, cylcopentane, n-hexane, cyclohexane, benzene, toluene and xylene.

13. The method of claim 11 wherein said absorbents are regenerated by displacing said adsorbed contaminants by other compounds that are adsorbed on said adsorbent preferentially over said contaminants.

14. The method of claim 1 wherein said production of alkyl aromatic compounds comprises at least the steps of:
   (a) reacting feed aromatics and feed olefins in a reaction section to produce a desired alkyl aromatic compounds, recoverable byproducts and unrecoverable byproducts;
   (b) isolating and recovering in a separation section said desired alkyl aromatic product;
   (c) recovering and recycling in said separation section unconverted feedstock and said recoverable byproducts; and
   (d) isolating and purging said unrecoverable products.

15. The method of claim 14 wherein said reaction section comprises an alkylation zone for reacting said feed aromatics and said feed olefins over a zeolite alkylation catalyst to produce a first alkyl aromatic component, recoverable byproducts, and unrecoverable byproducts, and a transalkylation zone for reacting recoverable byproducts with feed aromatics over a zeolite transalkylation catalyst to form additional alkyl aromatic component, recoverable byproducts and unrecoverable byproducts; and wherein the alkylation zone and the transalkylation zone each comprises one or more reaction zones.

16. The method of claim 15 wherein said alkylation zone and transalkylation zone are arranged sequentially, in series, with said alkylation zone located upstream and said transalkylation zone located downstream.

17. The method of claim 15 wherein said alkylation zone and transalkylation zone are arranged sequentially in series, with said transalkylation zone located upstream and said alkylation zone located downstream.

18. The method of claim 15 wherein said alkylation zone and transalkylation zone are arranged in parallel.

19. The method of claim 14 wherein said reaction section further comprises an isomerization zone for the production of dialkyl aromatic compounds wherein said isomerization zone comprises one or more reaction zones.

20. The method of claim 14 wherein said reaction section comprises a combined alkylation/transalkylation zone for reacting said feed aromatics, said feed olefin and said recycle recoverable byproducts to form alkyl aromatic compounds, recoverable byproducts and unrecoverable byproducts, said reaction taking place in the presence of a zeolite catalyst suitable for alkylation reactions and transalkylation reactions wherein said alkylation/transalkylation zone comprises one ore more reaction zones.

21. The method of claim 14 wherein said reaction section comprises a combined alkylation/isomerization zone for reacting said feed aromatics, said feed olefin and said recycle recoverable byproducts to form alkyl aromatic compounds, recoverable byproducts and unrecoverable byproducts, said reaction taking place in the presence of a zeolite catalyst suitable for alkylation reactions and isomerization reactions; wherein said combined alkylation/isomerization zone comprises one or more reaction zones.

22. The method of claim 1 wherein said feed olefin consists essentially of olefins containing 2 to 4 carbon atoms and said feed aromatics consist essentially of at least one member selected from the group consisting of benzene, toluene, ethylbenzene, xylenes, cumene, n-propyl benzene and butylbenzene isomers.

23. The method of claim 22 wherein said olefin feed is selected from the group consisting of ethylene and propylene and the aromatic feed consists essentially of benzene.

24. The method of claim 1 wherein said zeolite catalyst is selected from the group consisting of zeolite beta, zeolite Y, zeolite omega, ZSM-5, ZSM-12, MCM-22, MCM-36, MCM-49, MCM-56, MCM-58, MCM-68, Faujasite, Mordenite, porous crystalline magnesium silicates and zirconium phosphate.

25. A method for reactivating at least partially deactivated zeolite catalyst used in one or more reaction zones in a reaction section where reactions are carried out in liquid phase or partially liquid phase for the production of alkyl aromatic compounds by reacting at least an olefin containing from 2 to 5 carbon atoms with at least an aromatic compound, said catalyst reactivation process comprising the steps of:
   (a) stopping or substantially reducing at least one selected feed to the reaction zone(s); and introducing a catalyst reactivating agent into said reaction zone(s) at a weight hourly space velocity between about 0.02 $hr^{-1}$ and 200 $hr^{-1}$; and raising the reaction zone(s) temperature(s) to temperature(s) above the normal reaction zone(s) operating temperature(s) by about 10° C. to 200° C.;
   (b) allowing said at least partially deactivated catalyst to be at least partially reactivated in said reaction zone(s) at said elevated temperature(s) over a period of time between 1 hour and 30 days;
   (c) terminating flow of said catalyst reactivating agent; and re-establishing normal reaction zone(s) operating conditions and said selected reactor charge(s); and
   (d) resuming production of said alkyl aromatic compounds in said reaction zone(s).

26. The method of claim 25 wherein said olefin reactant comprises from 2 to 4 carbon atoms.

27. A method for reactivating zeolite catalyst, which catalyst is at least partially deactivated with feedstock contaminants, used in one or more reaction zones in a reaction section where reactions are carried out in liquid phase or partially liquid phase for the production of alkyl aromatic compounds by reacting at least an olefin containing from 2 to 5 carbon atoms with at least an aromatic compound, said catalyst reactivation process comprising the steps of:
   (a) stopping or substantially reducing at least one selected feed to the reaction zone(s); and introducing a catalyst reactivating agent into said reaction zone(s) at a weight hourly space velocity between about 0.02 $hr^{-1}$ and 200 $hr^{-1}$; and raising the reactor temperature to a temperature above the normal reaction zone(s) operating temperature(s) by about 10° C. to 200° C.;
   (b) allowing said at least partially deactivated catalyst to be at least partially reactivated in said reaction zone(s) at said elevated temperature(s) over a period of time between 1 hour and 30 days;
   (c) terminating flow of said catalyst reactivating agent; and re-establishing normal reaction zone(s) operating conditions and said selected reactor charge(s); and
   (d) resuming production of said alkyl aromatic compounds in said reaction zone(s).

28. The method of claim 27 wherein said feedstock contaminants are selected from the group consisting of basic materials, polar compounds, nitrogen-containing compounds and mixtures thereof.

29. A method for reactivating zeolite catalyst, which catalyst is at least partially deactivated with oligomers and/or other heavy compounds formed from olefins contained in the feedstock, used in one or more reaction zones in a reaction section in which the reactions are carried out in liquid phase or partially liquid phase for the production of alkyl aromatic compounds by reacting at least an olefin containing from 2 to 5 carbon atoms with at least an aromatic compound, said catalyst reactivation process comprising the steps of:
   (a) stopping or substantially reducing at least one selected feed to the reaction zone(s); and introducing a catalyst reactivating agent into said reaction zone(s) at a weight hourly space velocity between about 0.02 $hr^{-1}$ and 200 $hr^{-1}$; and raising the reaction zone temperature(s) to temperature(s) above the normal reaction zone(s) operating temperature(s) by about 10° C. to 200° C.;
   (b) allowing said at least partially deactivated catalyst to be at least partially reactivated in said reaction zone(s) at said elevated temperature(s) over a period of time between 1 hour and 30 days;
   (c) terminating flow of said catalyst reactivating agent; and re-establishing normal reaction zone(s) operating conditions and said selected reactor charge(s); and
   (d) resuming production of said alkyl aromatic compounds in said reaction zone(s).

* * * * *